United States Patent
Saly et al.

(10) Patent No.: US 9,382,270 B2
(45) Date of Patent: Jul. 5, 2016

(54) SUBSTITUTED SILACYCLOPROPANE PRECURSORS AND THEIR USE FOR THE DEPOSITION OF SILICON-CONTAINING FILMS

(71) Applicant: Applied Materials, Inc., Santa Clara, CA (US)

(72) Inventors: Mark Saly, Santa Clara, CA (US); David Thompson, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 14/876,057

(22) Filed: Oct. 6, 2015

(65) Prior Publication Data

US 2016/0031916 A1    Feb. 4, 2016

Related U.S. Application Data

(62) Division of application No. 14/560,517, filed on Dec. 4, 2014, now Pat. No. 9,177,783.

(60) Provisional application No. 61/914,199, filed on Dec. 10, 2013.

(51) Int. Cl.
| | |
|---|---|
| *C07F 7/00* | (2006.01) |
| *C07F 7/10* | (2006.01) |
| *H01L 21/02* | (2006.01) |
| *C23C 16/455* | (2006.01) |

(52) U.S. Cl.
CPC .............. *C07F 7/10* (2013.01); *C23C 16/45553* (2013.01); *H01L 21/0217* (2013.01); *H01L 21/0228* (2013.01); *H01L 21/02123* (2013.01); *H01L 21/02211* (2013.01); *H01L 21/02219* (2013.01); *H01L 21/02271* (2013.01); *H01L 21/02274* (2013.01)

(58) Field of Classification Search
CPC ........................................................ C07F 7/10
USPC ........................................................ 556/407
See application file for complete search history.

(56) References Cited

U.S. PATENT DOCUMENTS

| | | | |
|---|---|---|---|
| 5,186,718 | A | 2/1993 | Tepman et al. |
| 8,415,494 | B2 | 4/2013 | Jung |
| 2007/0299274 | A1 | 12/2007 | Meiere |
| 2009/0111284 | A1 | 4/2009 | Wang et al. |
| 2011/0159212 | A1 | 6/2011 | Ohno et al. |
| 2011/0313184 | A1 | 12/2011 | Tajima et al. |

FOREIGN PATENT DOCUMENTS

| | | |
|---|---|---|
| JP | S60-221575 | 11/1985 |
| JP | S60221575 | 11/1985 |
| KR | 10-2012-0131114 | 12/2012 |
| KR | 1020120131114 | 12/2012 |

OTHER PUBLICATIONS

Chen et al., Dalton Transactions (2011), 40(31), 7898-7907.*
14876057—STIC STN Search Results—Extract.*
Database Registry, SNT Database, CAS Registry No. 1251836-62-0 Nov. 2010, 2 pages.
PCT International Search Report and Written Opinion on PCT/US2014/068758, dated Mar. 11, 2015, 9 pages.
Boudjouk, Philip et al., "11. trans-1,1-Di-tert-Butyl-2,3-Dimethylsilirane and 2,2-Di-tert-Butyl-1,1,1-Triethyldisilane", *Inorganic Synthesis*, vol. 31 1997, 81-85.
Denk, Michael et al., "Synthesis and Structure of a Stable Silylene", *J. Am. Chem. Soc.* vol. 116 1994, 2691-2692.
Haaf, Michael et al., "Synthesis and reactivity of the stable silylene N,N'-di-tert-butyl-1,3-diaza-2-sila-2-ylidene", *Can. J. Chem.* vol. 78 2000, 1526-1533.
Seyferth, Dietmar et al., "7,7-Dimethyl-7-Siladispiro[2.0.2.1] Heptane Derivatives. The First Silacyclopropanes", *Journal of Organometallic Chemistry* vol. 122 1976, 311-328.
Database Registry, SNT Database, CAS Registry Number: 1251836-62-0 Nov. 2010, 2 pages.
Boudjouk, Philip et al., 11. trans-1,1-Di-tert-Butyl-2,3-Dimethylsilirane and 2,2-Di-tert-Butyl-1,1,1-Triethyldisilane, *Inorganic Synthesis*, vol. 31 1997, 81-85.
Denk, Michael et al., Synthesis and Structure of a Stable Silylene, *J. Am. Chem. Soc.* vol. 116 1994, 2691-2692.
Haaf, Michael et al., Synthesis and reactivity of the stable silylene N,N'-di-tert-butyl-1,3-diaza-2-sila-2-ylidene, *Can. J. Chem.* vol. 78 2000, 1526-1533.
Seyferth, Dietmar et al., 7,7-Dimethyl-7-Siladispiro[2.0.2.1] Heptane Derivatives. The First Silacyclopropanes, *Journal of Organometallic Chemistry* vol. 122 1976, 311-328.
Seyferth, Dietmar et al., Generation of Dimethylsilylene under Mild Conditions by the Thermolysis of Hexamethylsilirane, *Journal of the American Chemical Society*, vol. 97 No. 24, Communications to the Editor Nov. 26, 1975, 7162-7163.
Seyferth, Dietmar et al., Hexamethylsilirane. A Simple, Isolable Silacyclopropane, *Journal of the American Chemical Society* vol. 97 No. 8, Communications to the Editor Apr. 16, 1975, 2273-2275.
Seyferth, Dietmar et al., Silacyclopropenes I. Synthesis and Properties of Som Silacyclopropenes, *Journal of Organometallic Chemistry*, vol. 272 1984, 123-139.

\* cited by examiner

*Primary Examiner* — Porfirio Nazario Gonzalez
*Assistant Examiner* — Kofi Adzamli
(74) *Attorney, Agent, or Firm* — Servilla Whitney LLC

(57) ABSTRACT

Provided are silacyclopropane-based compounds and methods of making the same. Also provided are methods of using said compounds in film deposition processes to deposit films comprising silicon. Certain methods comprise exposing a substrate surface to a silacyclopropane-based precursor and a co-reagent in various combinations.

5 Claims, 2 Drawing Sheets

SUBSTITUTED SILACYCLOPROPANE PRECURSORS AND THEIR USE FOR THE DEPOSITION OF SILICON-CONTAINING FILMS

CROSS-REFERENCE TO RELATED APPLICATIONS

This application is a Divisional of U.S. patent application Ser. No. 14/560,517, filed Dec. 2, 2014, which claims priority to U.S. Provisional Application No. 61/914,199, filed Dec. 10, 2013, the entire disclosures of which are hereby incorporated by reference herein.

TECHNICAL FIELD

The present disclosure relates generally to methods of depositing thin films. In particular, the disclosure relates to processes for the deposition of films comprising silicon.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films with control and conformal deposition is atomic layer deposition (ALD), which employs sequential, surface reactions to form layers of precise thickness. Most ALD processes are based on binary reaction sequences which deposit a binary compound film. Because the surface reactions are sequential, the two gas phase reactants are not in contact, and possible gas phase reactions that may form and deposit particles are limited. Another method for deposition of films is chemical vapor deposition, in which two or more reagents are co-flowed to deposit a film over a substrate.

Silicon is a very important component in semiconductor processing. Currently no process exists for the deposition of silicon-containing materials (e.g., SiCN, SiN, SiBN, SiON, etc.) at low temperatures (i.e., less than about 400° C.) without the use of plasma co-reagents. This is because most silicon precursors have limited-reactivity towards chemisorption and/or common co-reagents, such as $NH_3$, $O_2$, $H_2O$. Furthermore, even if a silicon precursor has the requisite reactivity, it can be crucial to have quick reactions during half reaction cycles of ALD, or the growth rate will be too low to be practical for commercial applications. Additionally, while there are known silicon ALD/CVD precursors that contain halides, these can be problematic, as the halides can undesirably end up in the deposited film.

Accordingly, there is a need for new chemistries and methodology for the deposition of silicon-containing films which addresses one or more of the problems described above.

SUMMARY

A first aspect of the disclosure pertains to a compound having a structure represented by formula (IIIA-B), (IVA-B) or (VA-B):

(IIIA)
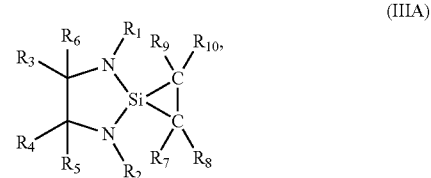

(IIIB)
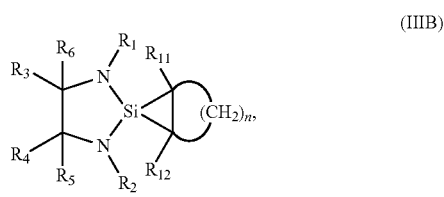

(IVA)
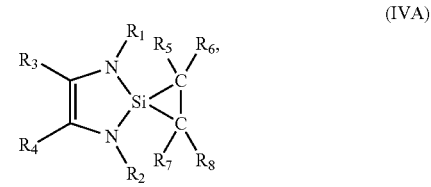

(IVB)
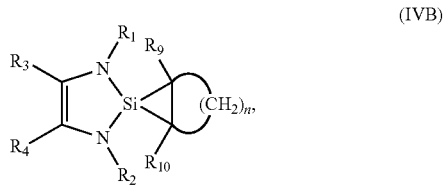

(VA)
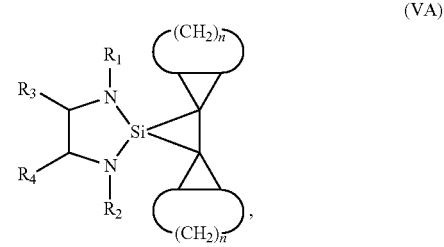

(VB)
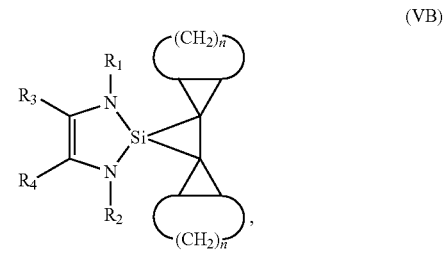

wherein each of $R_{1-12}$ is independently hydrogen, or a linear, branched or cyclic alkyl group with $C_{1-9}$, and n ranges from 2 to 6.

Another aspect of the disclosure pertains to a method of making the compounds of the first aspect, the method comprising reacting a compound having a structure represented by formula (VIA):

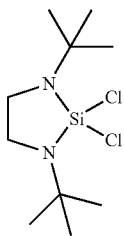

(VIA)

with a compound having a structure represented by formula (VII):

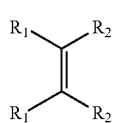

(VII)

wherein each $R_{1-2}$ are independently H, or $C_{1-9}$ linear, branched or cyclic alkyl group.

A third aspect of the disclosure pertains to a method of depositing a silicon-containing film. In one or more embodiments, method comprises exposing a substrate surface to a silicon precursor having a structure represented by:

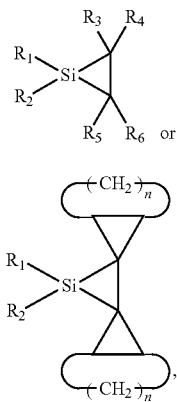

wherein each R, $R_1$ and $R_2$ are independently a negatively charged group or a saturated or unsaturated, linear or branched or cyclic group with 1-8 atoms selected from carbon and nitrogen, $R_{3-6}$ are each independently a saturated or unsaturated, linear or branched or cyclic group with 1-8 atoms selected from carbon and nitrogen and n ranges from 0 to 6. In some embodiments, the method further comprises exposing the substrate surface to a co-reactant to provide a silicon-containing film.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
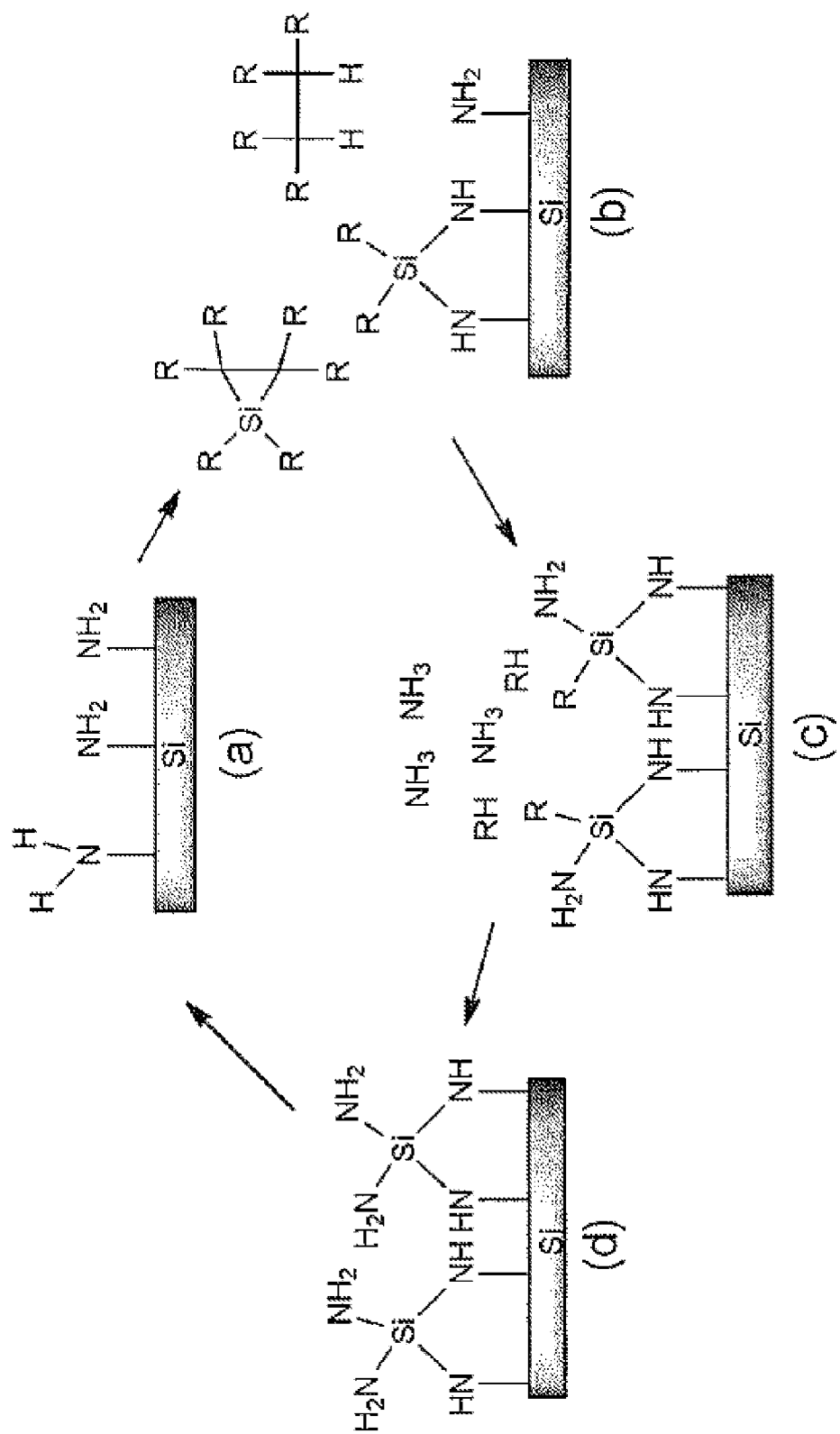
FIG. 1 shows an exemplary chemical mechanism of a method in accordance with one or more embodiments of the disclosure.

Before describing several exemplary embodiments of the disclosure, it is to be understood that the disclosure is not limited to the details of construction or process steps set forth in the following description. The disclosure is capable of other embodiments and of being practiced or being carried out in various ways. It is also to be understood that the complexes and ligands of the present disclosure may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

It has been discovered that silicon-containing films can be deposited using certain silicon precursors which are silacyclopropane-based. One or more of the embodiments described herein provide for the deposition of a silicon-containing film at relatively low temperatures (e.g., below 400° C.) without the need for plasma co-reagents. Silacyclopropane-based precursors may be used as-is, or alternatively may decompose to silylene to deposit silicon. Although silylenes are generally quite reactive and can be unstable and/or isolatable at room temperature, aspects of this disclosure provide for the silylene to be formed in situ (in an ampoule or in the chamber or at the surface) from a stable molecule (silacyclopropane-based molecules). Silylenes are thought to generate in situ by the decomposition of silacyclopropane-based molecules at or above a heated surface, or within an ampoule which are then used to create silicon containing films by ALD or CVD. Silylenes contain a lone pair on the silicon and will be reactive towards any co-reactant gas during ALD or CVD processes. It is thought that the in situ production of silylenes at the surface or above the surface will provide reactive silicon species for relatively fast (and therefore commercially viable) ALD reactions. Additionally, silylenes produced in situ will lead to the thermal deposition of halide-free silicon containing films at low temperatures by ALD or CVD, unlike currently used silicon precursors which contain halides.

Aspects of the disclosure therefore provide for the use of silacyclopropane-based molecules as precursors to low temperature deposition of silicon-containing thin films (e.g., SiN, SiCN, SiBN, $SiO_2$, etc.) with common ALD/CVD co-reactants such as $O_2$, $H_2O$ and/or $NH_3$. The co-reactants may also be enhanced by plasma in some embodiments, although it is not necessary.

Compounds

Accordingly, one aspect of the disclosure relates to certain compounds having a structure represented by formula (IIIA-B), (IVA-B) or (VA-B):

(IIIA)
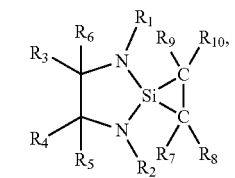

(IIIB)
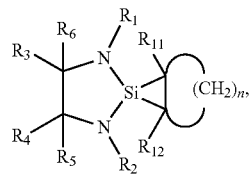

(IVA)
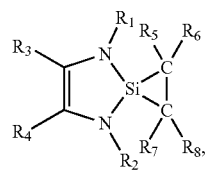

(IVB)
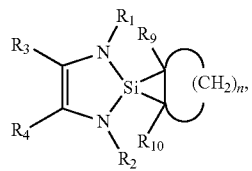

(VA)
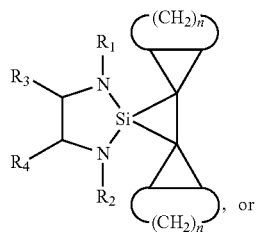

(VB)
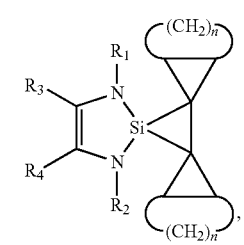

wherein each of $R_{1-12}$ is independently hydrogen, or a linear, branched or cyclic alkyl group with $C_{1-9}$, and n ranges from 2 to 6. In some embodiments, $R_3$ and $R_4$ are each hydrogen. In one or more embodiments, wherein $R_1$ and $R_2$ are each methyl.

In further embodiments, the compound has a structure represented by formula (IVC):

(IVC)
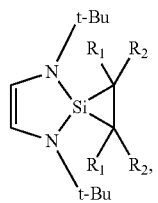

wherein each $R_{1-2}$ is independently a linear, branched or cyclic alkyl group with $C_{1-9}$.

Another aspect of the disclosure pertains to methods of producing the compounds described above. Generally, the process comprises reacting a compound having a structure represented by:

(VI-III)
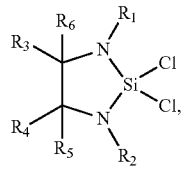

(VI-IV)
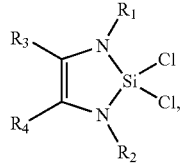

(VI-VA)
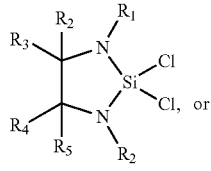

(VI-VB)
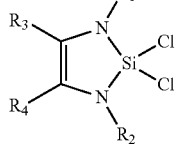

with a compound having a structure represented by:

(VII-IIIA)
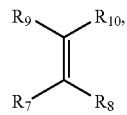

(VII-IIIB)
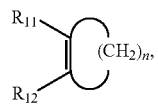

-continued (VII-IVA)

(VII-IVB)

(VII-V)

The specific combination will determine which precursors are ultimately synthesized. In some embodiments, reacting the compounds of formula (VI-III), (VI-IV), (VI-VA), or (VI-VB) with (VII-IIIA), (VII-IIIB), (VII-IVA), (VII-IVB), or (VII-V) comprises adding the compound of formula (VI-III), (VI-IV), (VI-VA), or (VI-VB) to a solution comprising lithium and the compound of formula (VII-IIIA), (VII-IIIB), (VII-IVA), (VII-IVB), or (VII-V). Exemplary synthetic schemes 1-3 follow below:

Scheme 1:

Scheme 2:

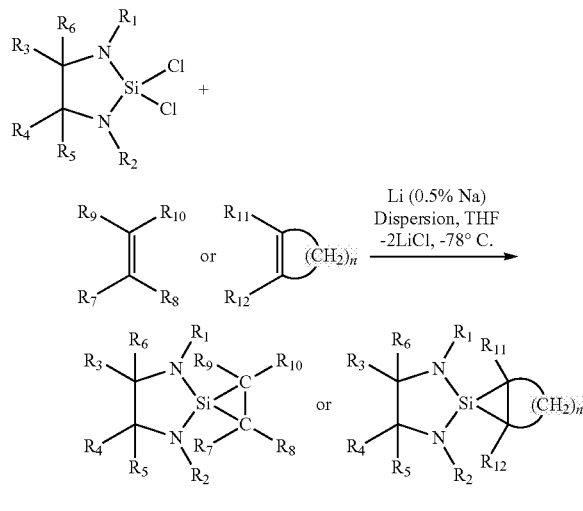

-continued

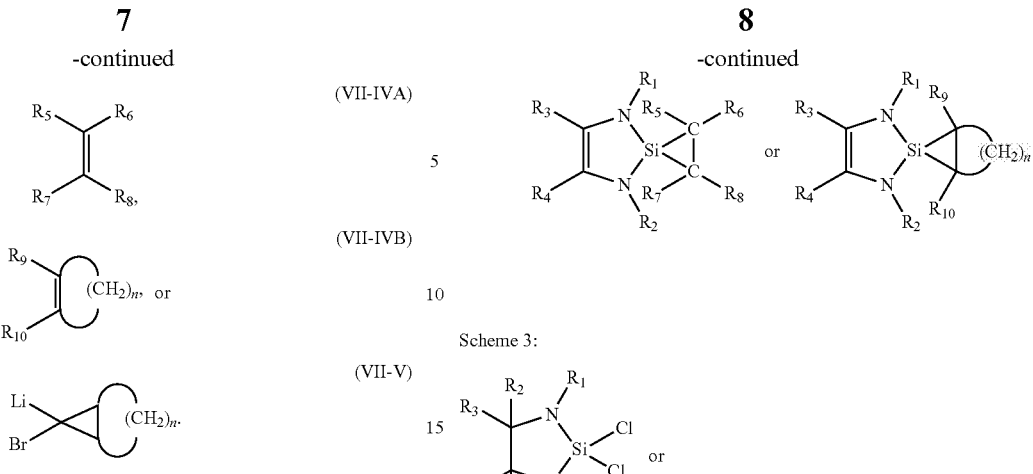

Scheme 3:

A specific example of precursor preparation is shown in Scheme 4 below:

Scheme 4:

Compound X can be synthesized according to literature procedure (see e.g., Haaf, M.; Schmedake, T. A.; Paradise, B. J.; West. R. *Can. J. Chem.* 2000, 1526-1533). The 2,3-dimethylbut-2-ene can be purchased, for example, from Sigma Aldrich. A 250 mL schlenk flask may be equipped with a stir bar was charged with Li (0.369 g, 0.0531 mol) and 100 mL of dry tetrahydrofuran (THF). The mixture can then be cooled to ~−78° C. in a dry ice/isopropanol bath. While stirring, the 2,3-dimethylbut-2-ene (4.47 g, 0.053 mol) may be slowly added to the flask containing the Li dispersion via syringe. A separate schlenk flask equipped with a stir bar can then be charged with compound X (4.77 g, 0.0177 mol) and 50 mL of dry THF. The compound X mixture may then be transferred via cannula to the flask containing the Li/2,3-dimethylbut-2- ene solution. After complete addition, the reaction mixture is stirred and slowly warmed up to room temperature by removing the dry ice/isopropanol bath. The mixture may be stirred overnight. The next day, stifling can be stopped to let the salts settle out. Next, the mixture may be filtered through a pad of celite via schlenk filtration techniques. The THF and other volatiles are removed under reduced pressure. This procedure would theoretically give 5 g (0.0177 mol) of Z.

Deposition Methods

Another aspect of the disclosure pertains to methods of depositing silicon-containing films. Any of the compounds described above, as well as additional compounds, may be utilized as silicon precursors. Accordingly, in one or more embodiments, the method comprises exposing a substrate surface to a silicon precursor having a structure represented by:

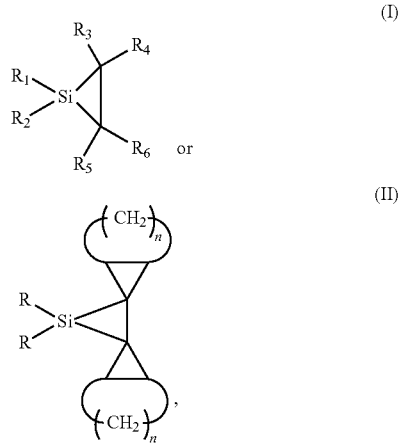

wherein R and $R_{1-2}$ are each independently a negatively charged group, $R_{3-4}$ are each independently saturated or unsaturated, linear or branched or cyclic group with 1-8 atoms selected from carbon and nitrogen, and n ranges from zero to 6. Formula (I) represents a general formula for silacyclopropane-based precursors. Formula (II) represents a general formula for silacyclopropane-based precursors containing cycloalkyl groups. In some embodiments, the substrate surface may then be exposed to a co-reactant to provide a silicon-containing film. In one or more embodiments, R and $R_{1-2}$ are each independently a 2-electron donor selected from the groups consisting of azido, cyano and isocyano. In some embodiments, R and $R_{1-2}$ are each independently saturated or unsaturated, linear or branched or cyclic group with 1-8 atoms selected from carbon and nitrogen, and n ranges from zero to 6. In one or more embodiments, R and $R_{1-2}$ are each independently selected from the group consisting of an amine, CN, $N_3$, Cl and NCO.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, silicon nitride, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal and/or bake the substrate surface. In addition to film processing directly on the surface of the substrate itself, in the present disclosure, any of the film processing steps disclosed may also be performed on an underlayer formed on the substrate as disclosed in more detail below, and the term "substrate surface" is intended to include such underlayer as the context indicates. Thus for example, where a film/layer or partial film/layer has been deposited onto a substrate surface, the exposed surface of the newly deposited film/layer becomes the substrate surface. In one or more embodiments, the substrate surface is terminated with —OH, —$NH_2$, or —NH functionality.

Co-reagents may be selected depending upon the film ultimately desired. In one or more embodiments, the co-reagent acts as a precursor for additional atoms. For example, in some embodiments, a film comprising silicon oxide ($SiO_2$) may be deposited using a co-reagent comprising an oxidant. In one or more embodiments, the oxidant comprises gaseous oxygen ($O_2$), ozone ($O_3$) or water ($H_2O$). In other embodiments, films comprising silicon nitride (SiN) may be deposited using a co-reagent comprising a nitrogen precursor. In one or more embodiments, the nitrogen precursor comprises ammonia ($NH_3$), hydrazine ($N_2H_4$) or an amine. In other embodiments, a boron precursor may be used to provide silicon boride (SiB) films. In yet other embodiments, a carbon precursor may be used to produce films comprising silicon carbide (SiC). Examples of suitable carbon precursor include carbon tetrachloride, alkanes, etc. Some co-reagents may act as precursors for more than one atom. In some embodiments, more than one co-reagent is used, wherein each deposits one type of atom. For example, a film comprising silicon, carbon and nitrogen (SiCN) may be deposited using carbon sources (e.g., alkane) as well as nitrogen sources (e.g., ammonia, hydrazine, etc.).

Silacyclopropane-based molecules are relatively reactive and can react exothermically with oxygen, water, alcohols, ammonia, hydrogen sulfide, carbon tetrachloride, or other such compounds at temperatures as low as room temperature. While not wishing to be bound to any particular theory, it is thought that the source of the high reactivity is related to the high ring strain of the silacyclopropane moiety. Therefore, it is expected that silacyclopropane-based precursors will react at elevated temperatures with oxygen, water, alcohols, ammonia, hydrogen sulfide, or carbon tetrachloride species to form silicon-based films deposited by ALD or CVD.

The following Equation 1 shows a common decomposition pathway for silacyclopropane-based molecules (1):

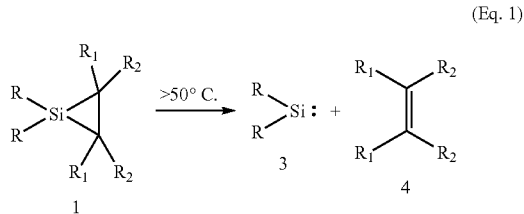

(Eq. 1)

The following Equation 2 shows a proposed decomposition pathway of a silacyclopropane-based complex containing the 1,4-di-tert-butyl-diaza-2-enyl-ligand (5):

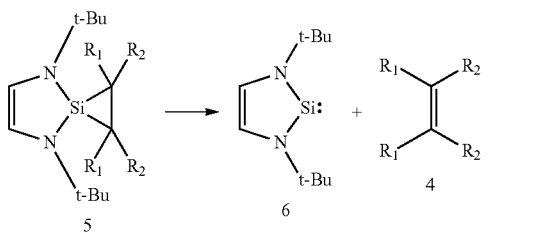

(Eq. 2)

The following Equation 3 shows the known decomposition pathway of hexamethylsilirane (7).

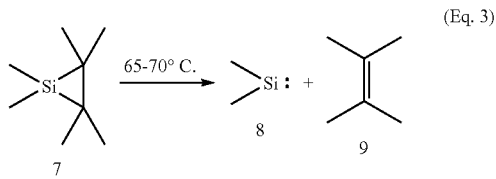

(Eq. 3)

Silacyclopropane-based molecules decompose at temperatures of greater than about 50° C. to form silylene and the corresponding alkene (4) (Equation 1) from which the silylenes can be used in an ALD/CVD reactor to create silicon containing films at low temperatures, free of halides. In one or more embodiments, it is also possible to tune the properties of the molecules by introducing various R groups or cyclic rings to the silacyclopropane. This can increase or decrease the overall reactivity of the silacyclopropane-based molecule and serve to increase or decrease the temperature at which the silylene is produced from the silacyclopropane-based precursor. The R substituents can also influence the stability of the silylenes that are produced in situ and the properties of the resulting alkene. For instance, during the decomposition of a silacyclopropane-based complex containing the 1,4-di-tert-butyl-diaza-2-enyl ligand (5) the formation of the stable silylene 1,3-di-tert-2,3-dihydro-1H-1,3-diazasilol-2-ylidene (6) would be expected (Equation 2). This silylene is stable in the solid state up to 220° C. It has been reported that heating hexamethylsilirane (7) between 65-70° C. results in dimethylsilylene (8) and 2,3-dimethyl-2-butene (9) (equation 2). Dimethylsilylene is very unstable and can only be detected in the gas phase. These examples demonstrate the versatility achieved by changing the R groups.

In one or more embodiments, the method comprises an atomic layer deposition (ALD) process. As used herein, "atomic layer deposition" refers to a process in which a substrate surface is exposed to alternate or sequential flows of a precursor and/or reagent. That is, the precursor and/or reagents may be flowed and/or exposed to the substrate surface sequentially or substantially sequentially. As used herein "substantially sequentially" refers to where the flows of the precursor and/or reagents do not overlap for a majority of the flow.

Therefore, in one exemplary embodiment, a silacyclopropane-based silicon precursor may be vaporized into an ALD chamber where the molecule can react with a surface group (OH, $NH_2$, etc) to provide a silyl terminated surface, followed by an inert purge. Then, the silyl terminated surface may be exposed to a co-reagent such as $O_2$, $H_2O$, $NH_3$, or plasma activated species ($O_2$, $H_2O$, $NH_3$, etc.) which would further react with the silyl species to form a layer of silicon-containing material. Repeating this cycle should afford films with precise thickness control. In an exemplary embodiment, the substrate temperature can be about 50-400° C.

FIG. 1 shows a possible mechanism of an example of self-limited film growth by an ALD process consisting of a silacyclopropane silicon precursor and ammonia co-reagent during one ALD cycle. The process in the figure begins with an amino ($NH_2$) terminated silicon surface that is heated (a). Next, the silacyclopropane-based precursor is introduced to the heated surface and reacts with the available $NH_2$ surface sites to form silicon-nitrogen bonds with the subsequent elimination of an alkane (b). After an inert gas purge, ammonia gas is introduced to the surface which reacts with the R groups to terminate the surface with amino groups and the free alkane is subsequently released (c) followed by an inert purge. Finally, the surface is NH2 terminated and ready for proceeding ALD cycles.

Figure 2:
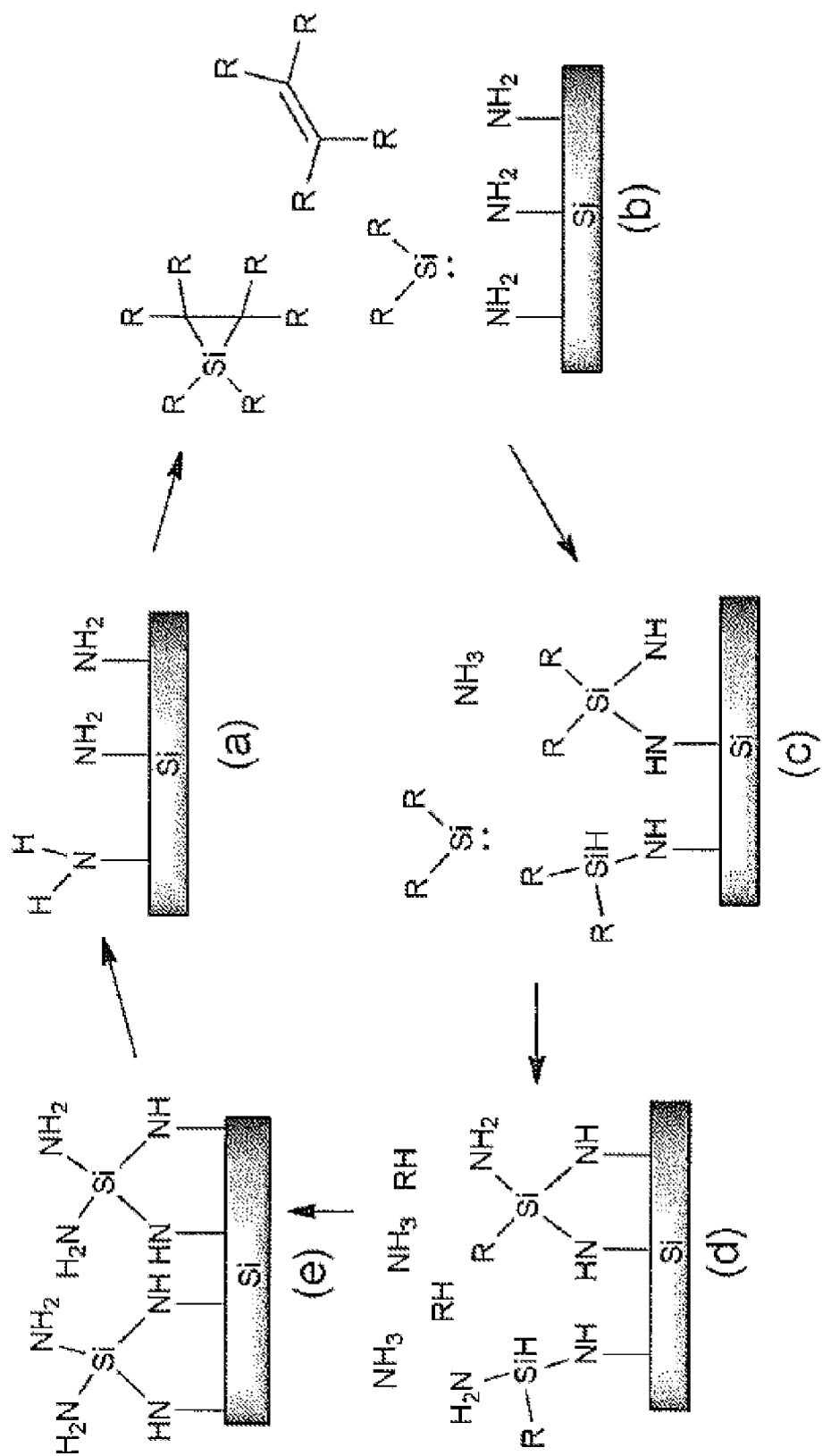
FIG. 2 shows an exemplary chemical mechanism of a method in accordance with one or more embodiments of the disclosure.

In one or more similar embodiments, the reactive species at the surface is the silylene. The silacyclopropane-based molecule undergoes thermal self-decomposition at the substrate surface to form a silylene-based molecule which than can react with the reactive surface sites. As long as the silylene does not react with itself, then self-limited film growth is thought to occur. An inert purge would follow the silacyclopropane-based molecule pulse, followed by treatment with a co-reagent gas, which would then react with the chemisorbed silicon species at the substrate surface. This will result in the formation of a silicon-containing film. The cycle may then be repeated until the desired film thickness is achieved. Repeating this cycle would lead to silicon containing films with precise thickness control. FIG. 2 shows a possible mechanism for self-limited film growth by in-situ production of the silylene from the silacyclopropane. In (a), a substrate surface with —$NH_2$ terminations are provided. In (b), a silicon precursor accordance with one or more embodiments of the disclosure is flowed in. The precursor decomposes to silylene-based molecule, which can react with the —$NH_2$ substrate surface terminations. In (c), the silylene-based molecule chemisorbs onto the substrate surface. In (d), ammonia is used as a co-reagent to form silicon nitride. In (e), the substrate surface is purged, leaving behind silicon nitride, with available —$NH_2$ terminations for additional deposition cycles.

In some embodiments, silylene is thermally generated in a heated ampoule at temperature of about 30 to 200° C. Then, the evolved silylene could be delivered to the deposition chamber for film formation. The silylene could form a film as described above.

In some embodiments, the method comprises a chemical vapor deposition (CVD) process. As used herein, "chemical vapor deposition" refers to a process in which a substrate surface is exposed to precursors and/or co-reagents simultaneous or substantially simultaneously. As used herein, "substantially simultaneously" refers to either co-flow or where there is overlap for a majority of exposures of the precursors. In one or more embodiments, any co-reagent is added with any one or more of the reactants.

Therefore, in one or more embodiments, the silacyclopropane-based molecule is vaporized into a reaction chamber and the reactant gas is co-flowed to form a silicon containing film. In some embodiments, the reactive species in the chamber and at the substrate surface is silylene. The silylene is generated from the silacyclopropane-based molecule that would decompose in the chamber at or above the substrate. The silylene species may then react with a co-reagent by chemical vapor deposition to form a silicon containing film.

In some embodiments, the substrate temperatures may range from about 50, 70, 100 to about 150, 200, 250, 300, 350, 400 or 500° C.

Again, in some embodiments, silylene is thermally generated in a heated ampoule at temperature of, for example, about 30 to 200° C. Then, the evolved silylene could be delivered to the deposition chamber for film formation. The silylene could form a film as described above.

Purges may be used after first, second and/or third precursors are flowed into the deposition chamber. That is, the substrate and chamber may be exposed to a purge step after stopping the flow of the given precursor gas. A purge gas may be administered into the processing chamber with a flow rate within a range from about 10 sccm to about 2,000 sccm, for example, from about 50 sccm to about 1,000 sccm, and in a specific example, from about 100 sccm to about 500 sccm, for example, about 200 sccm. The purge step removes any excess precursor, byproducts and other contaminants within the processing chamber. The purge step may be conducted for a time period within a range from about 0.1 seconds to about 8 seconds, for example, from about 1 second to about 5 seconds, and in a specific example, from about 4 seconds. The carrier gas, the purge gas, the deposition gas, or other process gas may contain nitrogen, hydrogen, argon, neon, helium, or combinations thereof. In one example, the carrier gas comprises nitrogen.

The reaction conditions for the reaction will be selected based on the properties of the film precursors and substrate surface, and any co-reagents. The deposition may be carried out at atmospheric pressure, but may also be carried out at reduced pressure. The vapor pressure of any co-reagents should be low enough to be practical in such applications. The substrate temperature should be low enough to keep the bonds of the substrate surface intact and to prevent thermal decomposition of gaseous reactants. However, the substrate temperature should also be high enough to keep the film precursors in the gaseous phase and to provide sufficient energy for surface reactions. The specific temperature depends on the specific substrate, film precursors, and catalyst used and pressure. The properties of the specific substrate, film precursors, and catalyst may be evaluated using methods known in the art, allowing selection of appropriate temperature and pressure for the reaction.

In one or more embodiments, the deposition is carried out at a temperature from about to 50 or 75 to about 500, 450, 400, 350, 300, 250, 200, 150, 125, or 100° C. In some embodiments, the deposition is carried out at a temperature in the range of about 50 to about 500° C., 70 to about 100° C., about 70 to about 125° C. or about 70 to about 125° C.

In some embodiments, one or more layers may be formed during a plasma enhanced atomic layer deposition (PEALD) process, although the relatively high reactivity of the precursors described herein generally do not require the assistance of a plasma-based process. In some processes, the use of plasma provides sufficient energy to promote a species into the excited state where surface reactions become favorable and likely. Introducing the plasma into the process can be continuous or pulsed. In some embodiments, sequential pulses of precursors (or reactive gases) and plasma are used to process a layer. In some embodiments, the reagents may be ionized either locally (i.e., within the processing area) or remotely (i.e., outside the processing area). In some embodiments, remote ionization can occur upstream of the deposition chamber such that ions or other energetic or light emitting species are not in direct contact with the depositing film. In some PEALD processes, the plasma is generated external from the processing chamber, such as by a remote plasma generator system. The plasma may be generated via any suitable plasma generation process or technique known to those skilled in the art. For example, plasma may be generated by one or more of a microwave (MW) frequency generator or a radio frequency (RF) generator. The frequency of the plasma may be tuned depending on the specific reactive species being used. Suitable frequencies include, but are not limited to, 2 MHz, 13.56 MHz, 40 MHz, 60 MHz and 100 MHz. Although plasmas may be used during the deposition processes disclosed herein, it should be noted that plasmas may not be required. Indeed, other embodiments relate to deposition processes under very mild conditions without a plasma.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or it can be moved from the first chamber to one or more transfer chambers, and then moved to the desired separate processing chamber. Accordingly, the processing apparatus may comprise multiple chambers in communication with a transfer station. An apparatus of this sort may be referred to as a "cluster tool" or "clustered system", and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. The details of one such staged-vacuum substrate processing apparatus are disclosed in U.S. Pat. No. 5,186,718, entitled "Staged-Vacuum Wafer Processing Apparatus and Method," Tepman et al., issued on Feb. 16, 1993. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, preclean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants after forming the layer on the surface of the substrate. According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

The substrate can be processed in single substrate deposition chambers, where a single substrate is loaded, processed and unloaded before another substrate is processed. The substrate can also be processed in a continuous manner, like a conveyer system, in which multiple substrate are individually loaded into a first part of the chamber, move through the chamber and are unloaded from a second part of the chamber. The shape of the chamber and associated conveyer system can form a straight path or curved path. Additionally, the processing chamber may be a carousel in which multiple substrates are moved about a central axis and are exposed to deposition, etch, annealing, cleaning, etc. processes throughout the carousel path.

During processing, the substrate can be heated or cooled. Such heating or cooling can be accomplished by any suitable means including, but not limited to, changing the temperature of the substrate support and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discreet steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

In atomic layer deposition type chambers, the substrate can be exposed to the first and second precursors either spatially or temporally separated processes. Temporal ALD is a traditional process in which the first precursor flows into the chamber to react with the surface. The first precursor is purged from the chamber before flowing the second precursor. In spatial ALD, both the first and second precursors are simultaneously flowed to the chamber but are separated spatially so that there is a region between the flows that prevents mixing of the precursors. In spatial ALD, the substrate must be moved relative to the gas distribution plate, or vice-versa. Use of the terms "expose to a substrate surface" and "flow" is intended to encompass both processes.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A compound having a structure represented by formula (IIIA-B), (IVA-B) or (VA-B):

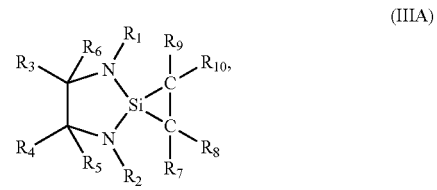

(IIIA)

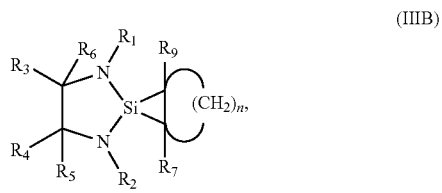

(IIIB)

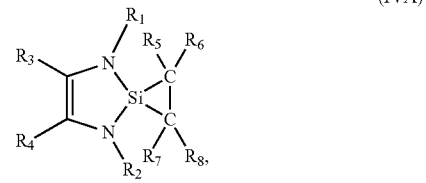

(IVA)

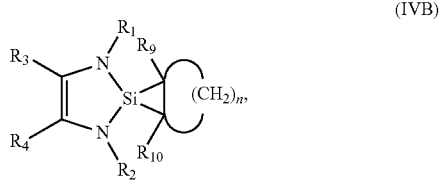

(IVB)

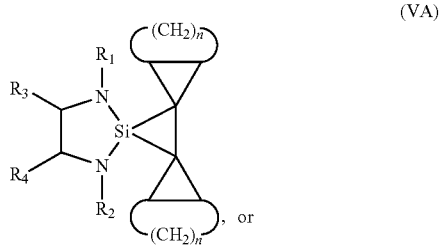

(VA)

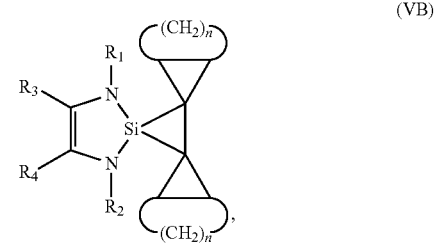

(VB)

wherein $R_1$ and $R_2$ are each methyl, and each of $R_{3-12}$ is independently hydrogen, or a linear, branched or cyclic alkyl group with $C_{1-9}$, and n ranges from 2 to 6.

2. A compound having a structure represented by formula (IVC):

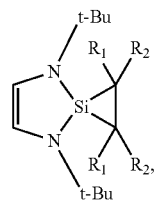
(IVC)

wherein each R1-2 is independently a linear, branched or cyclic alkyl group with C1-9.

3. A method of making the compound of claim 1, the method comprising: reacting a compound having a structure represented by formula (VI-III), (VI-IV), (VI-VA) or (VI-VB):

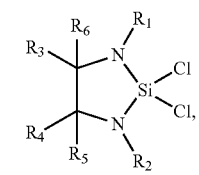
(VI-III)

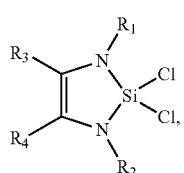
(VI-IV)

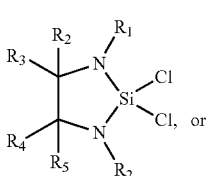
(VI-VA)

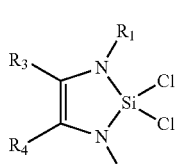
(VI-VB)

with a compound having a structure represented by:

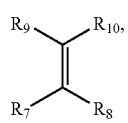
(VII-IIIA)

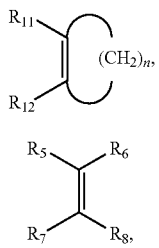
(VII-IIIB)

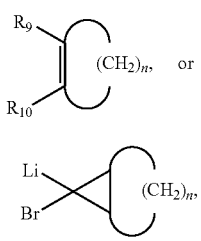
(VII-IVA)

(VII-IVB)

(VII-V)

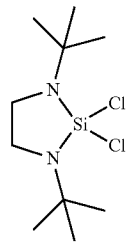

wherein reacting the compounds of formula (VI-III), (VI-IV), (VI-VA), or (VI-VB) with (VII-IIIA), (VII-IIIB), (VII-IVA), (VII-IVB), or (VII-V) comprises adding the compound of formula (VI-III), (VI-IV), (VI-VA), or (VI-VB) to a solution comprising lithium and the compound of formula (VII-IIIA), (VII-IIIB), (VII-IVA), (VII-IVB), or (VII-V) and each R1-2 is methyl.

4. The method of claim 3, wherein the compound having a structure represented by formula (VI) comprises a compound having a structure represented by formula (VIA):

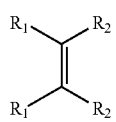

and the compound having the structure represented by formula:

$$\begin{array}{c} R_1 \\ R_1 \end{array} \!\!\!\!\!\!\!\!\!\!\!\!\!\!\!\!\!\!\!\!\!\!\!\!\!\!\!\!\!\!\!\!\!\!\!\!\! \begin{array}{c} R_2 \\ R_2 \end{array}$$

wherein each $R_{1-2}$ is independently H, or $C_{1-9}$ linear, branched or cyclic alkyl group.

5. The method of claim 4, wherein each $R_{1-2}$ is methyl.

* * * * *